United States Patent [19]
Young et al.

[11] Patent Number: 5,536,266
[45] Date of Patent: Jul. 16, 1996

[54] TOOL FOR REMOVAL OF PLASTICS MATERIAL

[75] Inventors: Michael J. R. Young, Ashburton; Brian R. D. P. Bradnock, Radlett, both of United Kingdom

[73] Assignee: Orthosonics, Ltd., Ashburton, United Kingdom

[21] Appl. No.: 404,174

[22] Filed: Mar. 6, 1995

Related U.S. Application Data

[63] Continuation-in-part of Ser. No. 330,256, Oct. 27, 1994, abandoned, and a continuation of Ser. No. 199,112, Feb. 22, 1994, abandoned, which is a continuation-in-part of Ser. No. 111,644, Aug. 25, 1993, abandoned, said Ser. No. 330,256, is a continuation of Ser. No. 111,644, filed as PCT/GB92/01553, Aug. 24, 1992.

[30] Foreign Application Priority Data

Aug. 24, 1991 [GB] United Kingdom .................. 9118307

[51] Int. Cl.⁶ .......................... A61B 17/38; A61B 17/32; A61B 17/00; A61F 2/32
[52] U.S. Cl. .................. 606/27; 606/84; 606/92; 606/169
[58] Field of Search ................. 606/79, 84, 85, 606/86, 99, 169, 171

[56] References Cited

U.S. PATENT DOCUMENTS

| | | |
|---|---|---|
| 3,794,040 | 2/1974 | Balamuth . |
| 4,004,581 | 1/1977 | Heimke et al. .......................... 606/81 |
| 4,023,572 | 5/1977 | Weigand et al. .......................... 606/81 |
| 4,248,232 | 2/1981 | Engelbrecht et al. . |
| 4,425,115 | 1/1984 | Wuchinich . |
| 4,696,292 | 9/1987 | Heiple ..................................... 606/79 |
| 4,832,683 | 5/1989 | Idemoto et al. .......................... 606/79 |
| 4,873,969 | 10/1989 | Huebsch . |
| 5,019,083 | 5/1991 | Klapper et al. . |
| 5,045,054 | 9/1991 | Hood et al. . |
| 5,064,426 | 11/1991 | Huebsch . |
| 5,167,619 | 12/1992 | Wuchinich . |
| 5,190,548 | 3/1993 | Davis ..................................... 606/79 |
| 5,203,653 | 4/1993 | Kudla ..................................... 606/81 |
| 5,205,817 | 4/1993 | Idemoto et al. .......................... 606/169 |
| 5,318,570 | 6/1994 | Hood et al. .............................. 606/99 |

FOREIGN PATENT DOCUMENTS 2229660  1/1990  United Kingdom .

OTHER PUBLICATIONS

Cencise Encyclopedia of Polymer Science and Engineering, 1990.

Primary Examiner—Jessica J. Harrison
Assistant Examiner—Michael O'Neill
Attorney, Agent, or Firm—Hopgood, Calimafde, Kalil & Judlowe

[57] ABSTRACT

A tool for use in removing plastics material from a hole comprises a work surface adapted to contact the material. A piezo-electric transducer is operatively connected through a work horn and causes the work surface to vibrate ultrasonically and thereby to heat locally the plastics material. A cavity is adapted to receive heated plastics material. The cavity has communication with a working zone adjacent the work surface. The work surface comprises an elongate boring member and rearwardly thereof a substantially annular cutting edge; the working zone communicates with the cavity via apertures disposed between the boring member and the annular cutting edge.

31 Claims, 5 Drawing Sheets

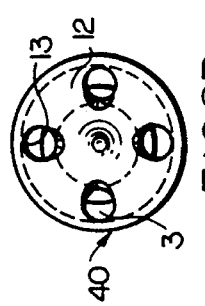
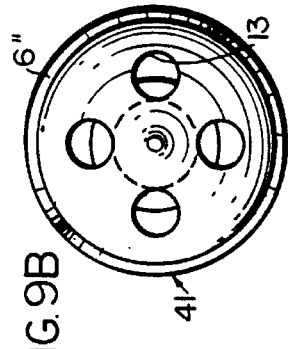
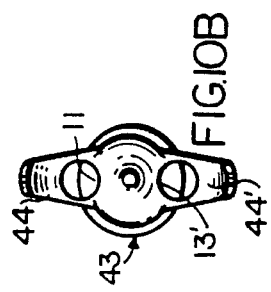
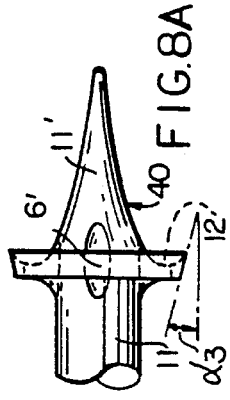
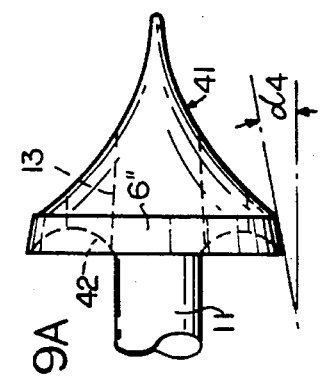
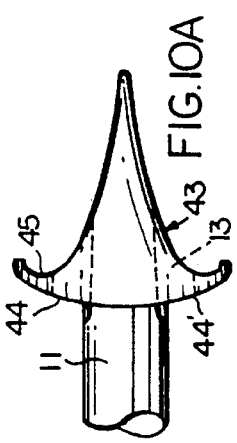
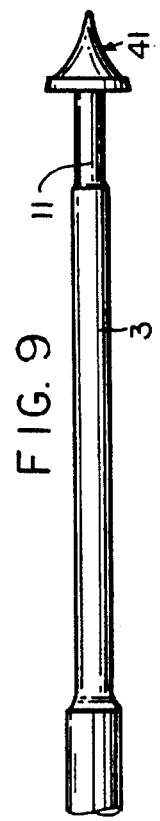
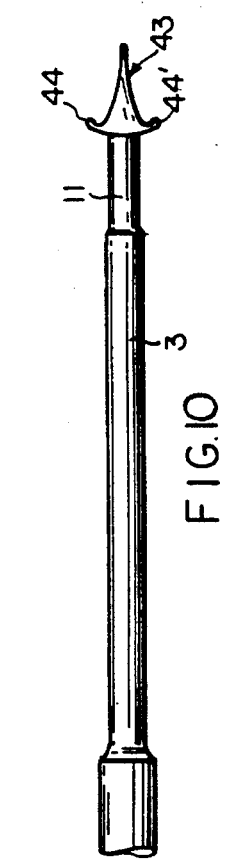
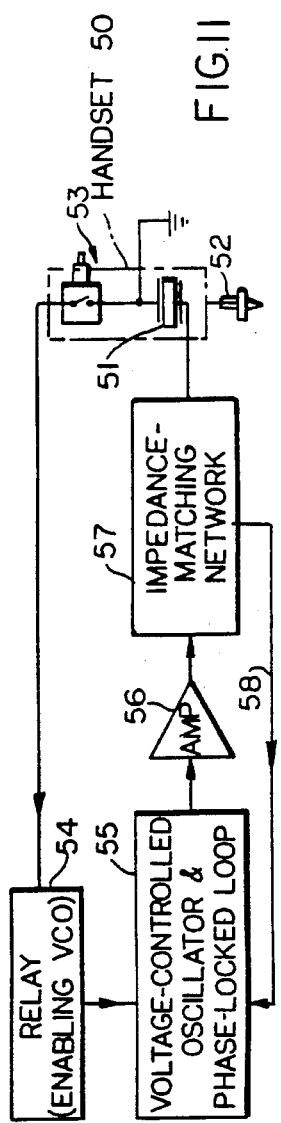

5,536,266

TOOL FOR REMOVAL OF PLASTICS MATERIAL

RELATED CASE

This application is a continuation-in-part of pending application Ser. No. 08/330,256, filed Oct. 27, 1994, now abandoned, and a continuation of pending application Ser. No. 08/199,112, filed Feb. 22, 1994, now abandoned; and said continuation-in-part pending application is a continuation of pending application Ser. No. 08/111,644, filed Aug. 25, 1993, now abandoned; and said continuation pending application is a continuation-in-part of pending application Ser. No. 08/111,644, filed Aug. 25, 1993, now abandoned, which is a National application based on PCT/GB92/01553.

BACKGROUND OF THE INVENTION

The present invention relates to an improved tool for use in removal of plastics material. A tool of this general type is disclosed in our UK Patent No. 2,229,660 and in our U.S. Pat. No. 5,151,019, but further improvements have been discovered. The tool is particularly, but not exclusively, useful in removing plastics cement from such bores in bones as may be used in hip, or other joint, replacements (hereinafter referred to, for convenience, as hip joint replacements).

In a hip joint replacement operation, a metal implant is provided with a long projection which is inserted into a hole drilled in the medulla of the femur and is held firmly in place by means of a plastics cement. On average, such replacements can be expected to last five to ten years. However, due to repetitive shearing forces during daily use, either the bone/cement interface or the cement/metal interface may weaken and the implant will become loose, requiring revision. Sometimes, the metal of the hip replacement may fracture or the plastics components may wear out. In these cases, revision is necessary although in most cases the bone/cement interface usually remains quite strong.

In order to revise any loose or damaged implant, all or most of the plastics cement must be removed before inserting a new prosthesis and re-cementing. Removal of the old cement presents a number of difficulties. It is time-consuming and may cause fracturing of the bone. It involves the careful and tedious use of hand tools such as hammers and cement cutting chisels. High speed burrs have been used, but they frequently perforate the bone and make recementing more difficult and not so effective.

BRIEF STATEMENT OF THE INVENTION

It is an object of the present invention to provide an improved tool for removal of plastics material such as cement from a bore, particularly one in a bone, which overcomes the above disadvantages.

According to a first aspect of the present invention there is provided a tool for use in removing plastics material from a hole comprising a work surface adapted to contact said material, piezo-electric transducer means operatively connected through a work horn to said work surface to cause it to vibrate ultrasonically and thereby to heat locally said plastics material, cavity means adapted to receive said heated plastics material, means to contact said cavity means to a working zone adjacent said work surface, wherein the work surface comprises an elongate boring member and rearwardly thereof a substantially annular cutting edge, said working zone being connected to said cavity means by means of apertures disposed between said boring member and said annular cutting edge.

According to a second aspect of the present invention there is provided a tool for use in removing plastics material from a hole comprising a work surface adapted to contact said material, piezo-electric transducer means operatively connected through a work horn to said work surface to cause it to vibrate ultrasonically and thereby to heat locally said plastics material, cavity means adapted to receive said heated plastics material, means to contact said cavity means to a working zone adjacent said work surface, wherein the work surface includes at least one cutting fin extending radially outwardly of the annular cutting edge. Preferably, four cutting fins are provided, disposed substantially equi-angularly around the periphery of the annular cutting edge.

The cutting fins are particularly useful for renewing cement at the proximal end of the femur. The fins cut grooves in the cement almost to the endosteal surface of the femur, allowing the cement subsequently to be removed in pieces with ease.

According to a third aspect of the present invention there is provided a tool for use in removing plastics material from a hole comprising a work surface adapted to contact said material, piezo-electric transducer means operatively connected through a work horn to said work surface to cause it to vibrate ultrasonically and thereby to heat locally said plastics material, cavity means adapted to receive said heated plastics material, means to contact said cavity means to a working zone adjacent said work surface, wherein at least the piezo-electric transducer means is sealingly encased in a first enclosure of waterproof plastics material and exterior thereof a second enclosure of stainless steel or the like material.

Advantageously, the waterproof plastics material is an acetal plastics material.

The arrangement of the third aspect allows the tool to be autoclaved or otherwise sterilized for use for another patient.

BRIEF DESCRIPTION OF THE DRAWINGS

Embodiments of the present invention will now be more particularly described by way of example and with reference to the accompanying drawings, in which:

FIG. 8 is a view in side elevation of a tool element of the invention, representing a modification of the embodiment of FIGS. 1 and 2;

FIG. 8A is an enlarged fragmentary side elevation of the distal or working end of the tool element of FIG. 8;

FIG. 8B is an end view of the tool element of FIG. 8, to the enlarged scale of FIG. 8A;

FIG. 9 is a side elevation, similar to that of FIG. 8, but for another embodiment;

FIG. 9A is an enlarged fragmentary view as in FIG. 8A, but applicable to the embodiment of FIG. 9;

FIG. 9B is an end view similar to that of FIG. 8B, but for the embodiment of FIG. 9;

FIG. 10 is a side elevation, similar to that of FIG. 8, but for a further embodiment;

FIG. 10A is an enlarged fragmentary side elevation, similar to that of FIG. 8A, but applicable to the embodiment of FIG. 10;

FIG. 10B is an end view similar to that of FIG. 8B, but for the embodiment of FIG. 10; and FIG. 11 is an electrical block diagram for excitation circuitry to drive any of the foregoing embodiments of the invention.

DETAILED DESCRIPTION

Figure 1:
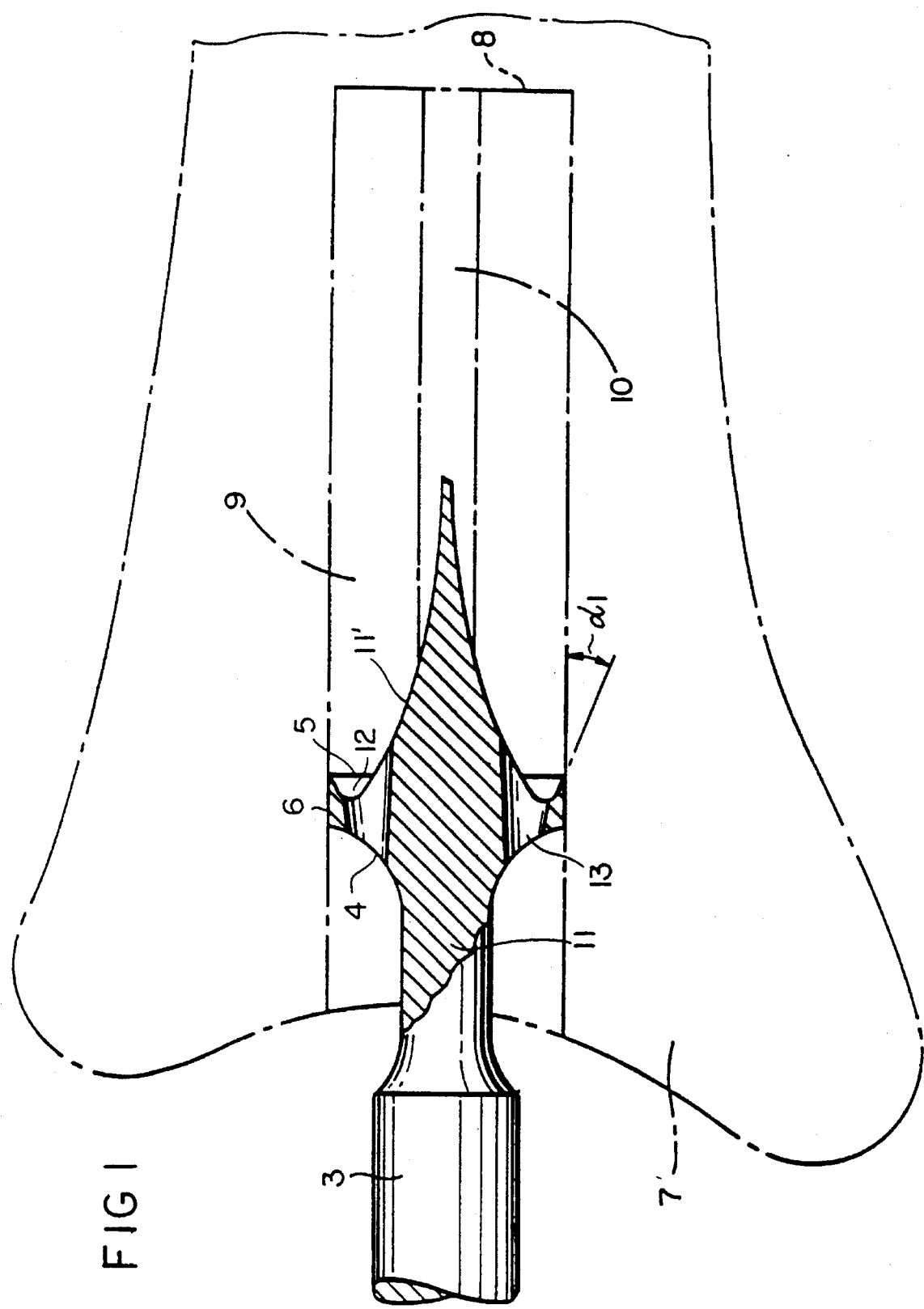
FIG. 1 is a schematic side elevation, shown partially in cross-section, of a tool element representing a first embodiment of the invention.
Figure 5:
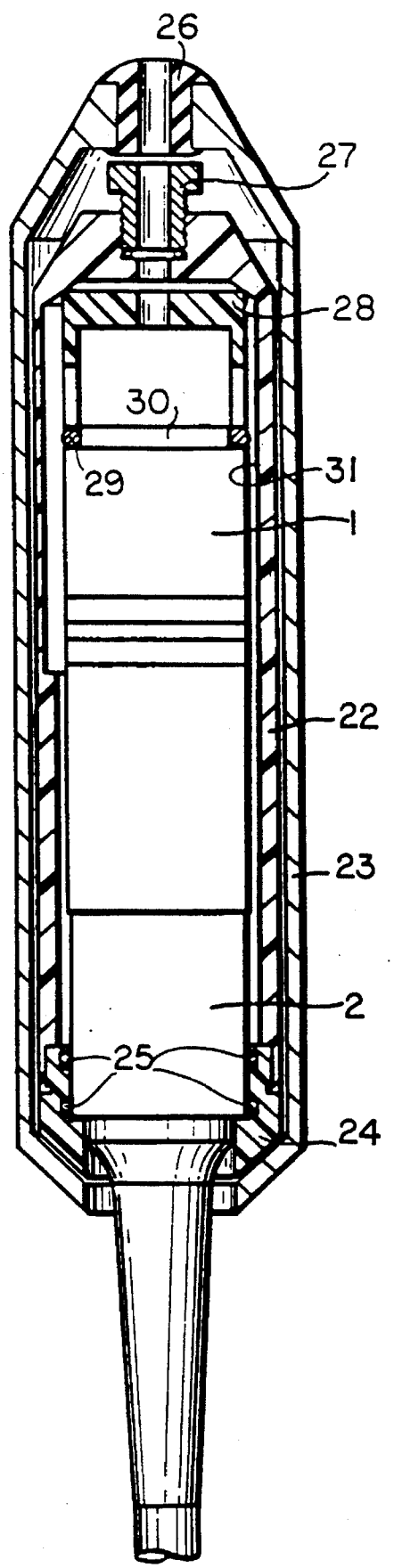
FIG. 5 is a simplified longitudinal section of a piezoelectric driver for tool elements of the invention.

Referring now to the drawings, there is shown in the drawings a tool comprising a piezo-electric ceramic transducer 1 (FIG. 5), connected along a longitudinal axis to a coupling horn 2, which in turn is connected along the longitudinal axis to a work horn 3 (FIGS. 1 and 5). At the far end of the work horn 3 is a cavity 4 surrounded by the cylindrical bore generated by distal advance of an annular cutting edge 5.

The cutting edge 5 is the distal circular edge of a radial flange formation which extends outward from a stem or body portion 11 of reduced diameter, as compared to the diameter of the adjacent work-horn portion 3; in the distal direction from the flange formation, the stem portion projects as a convergent generally conical formation 11' having a base end of less diameter than the flange. As shown, the generally conical formation 11' is a slightly concave and somewhat parabolic surface of revolution which, in the region of its base, forms an annular recess 12 having a radially outer wall surface that intersects the cylindrical surface 6 at an acute angle $\alpha_1$, to define the circular cutting edge 5. The angle $\alpha_1$ is suitably in the range 20° to 35°. Plural angularly spaced passages 13 extend longitudinally through the web of the flange formation, to permit plastics material softened at the distally-facing or work-surface end to flow through passages 13 and thus to communicate with cavity 4, for temporary accumulation in the cavity 4 which exists circumferentially around stem/body portion 11.

The length of the piezo-electric ceramic transducer 1 is half a wavelength, the length of the coupling horn 2 is a full wavelength, while the length of the work horn 3 (which includes the annular cutting edge 5) is an integral number of half wavelengths, ensuring that the total probe length can penetrate to the required depth. The term "wavelength" is used to represent the wavelength of the ultrasonic wave generated by the piezo-electric ceramic transducer in the material concerned. The preferred material for the work horn and annular cutting edge is titanium or an alloy thereof. At an ultrasonic vibrational frequency in the region of 30–35 kHz, the wavelength of the ultrasonic wave in the titanium alloy is in the region of 70–90 mm.

It is known that heating can occur at the interface between a vibrating tool and plastics material, the heating being sufficient to melt the plastic. The present invention utilizes this effect to drill a hole into the plastics material.

The plastics cement material used for hip joint replacements is generally a powder of polymethylmethacrylate beads of diameter less than 100 μm held together in situ by a polymerized methyl methacrylate monomer. This material is prone to creep and is susceptible to localized heating on ultrasonic vibration. The property of creep may be utilized in that, during removal of a core of plastics cement material, the existing cement which remains may be forced into improved engagement with fissures or surface imperfections in the bone by virtue of the ultrasonic vibrations imparted to the cement, and thereby stabilize the interface.

At the work surface, the annular cutting edge 5 can be manipulated by the user of the tool to enable the bore diameter to be widened or, by applying pressure to one side of the tool, to create a hole of oval profile.

The present invention is described with reference to removing a plastics cement from a hip joint replacement during revision of the prosthesis. In this case, the hip bone or femur 7 has a blind hole 8 filled with plastics cement 9 which had originally surrounded the prosthesis, but which has a void 10 where the prosthesis used to be.

In order to operate the tool, the tip 11' is inserted a short distance into the plastics material cement 9 and pushed thereinto for about 5–10 mm, as the plastics material softens under the effect of the ultrasonic vibrations. At this point, a core of softened but relatively stiff cement will have been driven through passages 13 to fill the work horn cavity 4.

The tool can be removed to dislodge and discard accumulated plastics material from the work-horn cavity 4, and the sequence is then repeated until the cement is removed from the bore of hole 8 to an appropriate depth. It would be possible to incorporate a small intrascope coaxially within an axial duct in order to facilitate visual inspection of the cutting operation.

Use of the tool embodying the present invention results in a much faster cutting operation and also allows the possibility of leaving intact a thin layer of cement which is characteristically well-bonded to the living bone tissue when revising damaged but not loose implants. If the cement is already well-bonded, the strength of the revised implants would be significantly improved. The apparatus also may permit improved bonding between bone and existing cement. Whereas the existing methods of revision of a hip joint prosthesis may have required several hours to remove the existing cement, for all of which the patient must be anaesthetized, the present invention allows removal of existing cement, at least sufficient for revision, within a period of less than one hour. The work horn 3 may be curved to suit penetration of a curved hole in a medulla or similar bone.

Figure 3:
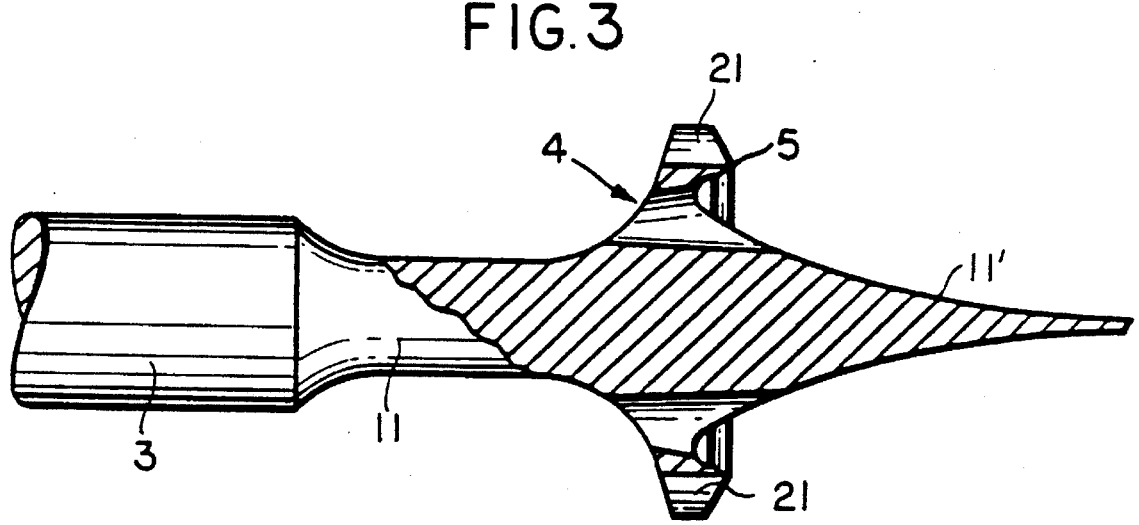
FIG. 3 is a schematic side elevation, partially in cross section, of an end portion of the tool element of a second embodiment of the invention.
Figure 4:
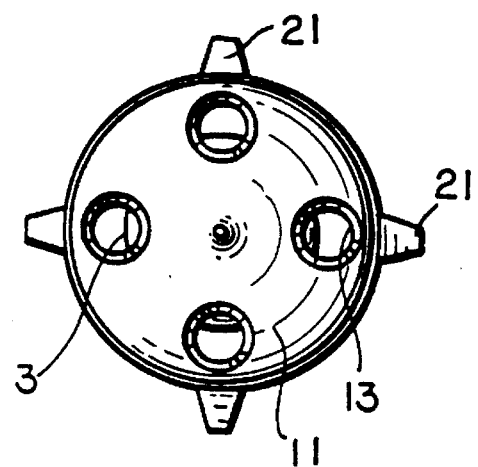
FIG. 4 is an end elevation of the tool element of FIG. 3.

For use at or adjacent the proximal end of the femur, it may be necessary to remove a core of cement of larger diameter. In this case, as shown in FIGS. 3 and 4, four external fins 21 are provided to cut grooves in this thicker cement. Once the tool has been withdrawn, the pieces of cement remaining between the grooves may be removed with ease.

Figure 6:
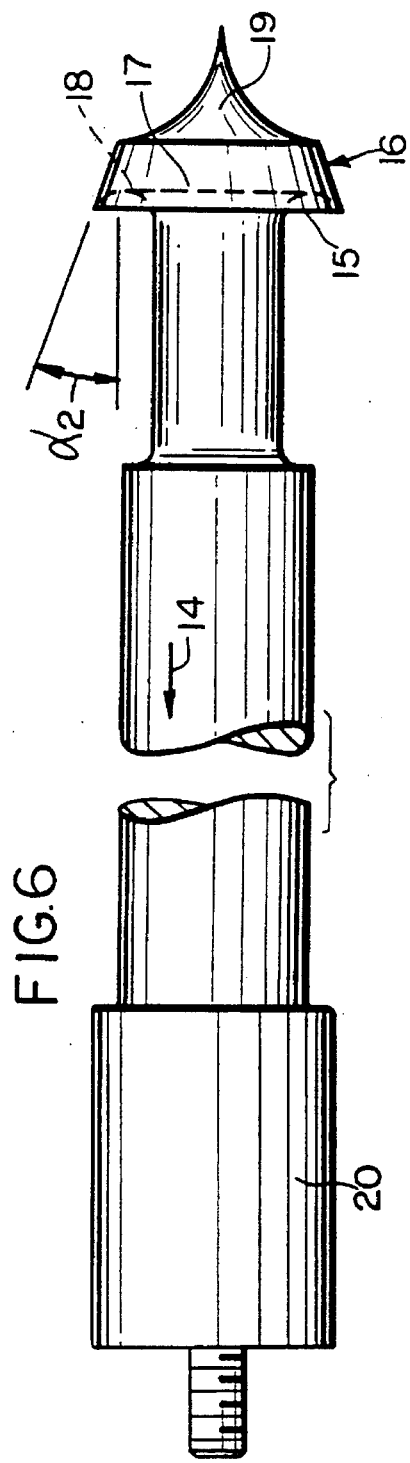
FIG. 6 is a fragmentary view in side elevation showing the working end of a third tool embodiment of the invention.

Referring now to FIG. 6, there is shown a tool element in the form of a scraper which has a sharp cutting edge 15 on the reverse or proximal side of a head flange 16, with a generally conically convergent end 19 projecting beyond flange 16. The cutting edge 15 is formed at the proximal edge of a frusto-conical surface 17, the slope $\alpha_2$ of which critically determines the controlled cutting action of the scraper. There are no connecting passages between front and rear faces of the flange 16; but, as the tool element is pulled in the proximal direction of the arrow 14 in FIG. 6, the edge 15 cuts into the cement on one side of the femoral cavity, and the removed material collects in an annular recess 18 behind the flange. This mechanism permits removal of discrete volumes of cement to ensure complete preparation of the endosteal surface, ready for recementing.

Figure 2:
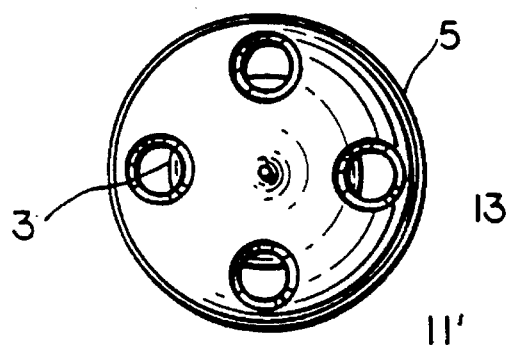
FIG. 2 is an end elevation of the tool element of FIG. 1.

The optimum angle $\alpha_2$ is between 20° and 25°; this has been found to permit cement removal safely and easily, with the application of only light force. The instrument is of particular use in cases of severe bone resorption which has left areas of extreme weakness in the femur. Great care is required to avoid perforation or fracture of the femur under these circumstances using conventional instruments. This embodiment of the invention achieves this difficult objective without risk. The reverse scraper is also of great use when preparing access to the distal plug and generally precedes the piercing operation effected with the a multi-port instrument, exemplified by FIGS. 1 and 2.

As shown in FIG. 5, the piezo-electric transducer part of the tool may be encased, first in an inner layer 22 of acetal plastics material and then in an outer layer or casting 23 of stainless steel; an annular plastics cap 24 closes the distal end of the inner casing 22 and is shown with O-ring seals 25 for resilient engagement to and mechanically isolating support of the coupling horn 2 when in ultrasonic oscillation. This arrangement will allow the tool to be autoclaved or otherwise sterilized in order to permit its use on further patients.

A grommet 26 and a gland nut 27 at the proximal end of the tool of FIG. 5 provide sealed passage for a mechanically isolated electric cable (not shown) for excitation of transducer 1, and a suitably apertured cup 28 that is seated in the proximal end of the inner casing 22 provides, at an O-ring 29, resilient axial isolation of the transducer while also radially and resiliently supporting the reduced end 30 of the transducer via the bore 31 of inner casing 22. As shown, one or more local longitudinal grooves, as at 32, in bore 31 provide passage for excitation and control wiring to the piezoelectric means of transducer 1.

Figure 7:
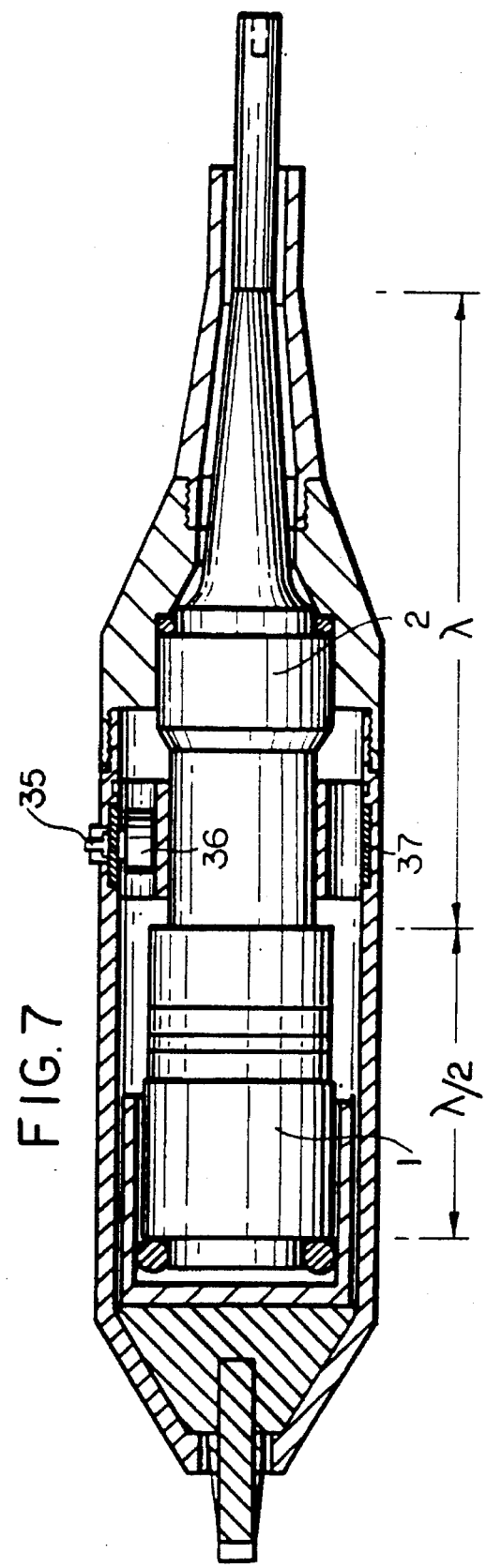
FIG. 7 is a view similar to FIG. 5 for a further tool-driven embodiment of the invention.

As shown in FIG. 7, the handset or tool-driving part of the tool bit may also incorporate a switch 36 and still be autoclavable.

The design philosophy takes account of the conditions prevailing in operating theatres and in particular the strict sterilization requirements. Several sizes and shapes of oscillatory instrument should ideally be available to the surgeon and a particular case might demand very specialized probe designs. Whereas it is possible to interchange probes on a single handset, as suggested by a threaded horn-connector element 20 in FIG. 6, this procedure is not only inconvenient but results in reduced efficiency of the system if the critical probe/horn interface becomes contaminated with foreign matter. It is desirable therefore to provide a number of independent handsets, each having its own different tool element, thus providing the surgeon with the opportunity for immediate tool selection and use, without the need for reconnection or adjustment of switching functions. This dictates the use of a switch incorporated in each handset. Since the handset and cable assembly must be suitable for autoclave sterilization, the switch assembly requires a special seal design to withstand the temperature and pressure conditions encountered during the sterilization process.

FIG. 7 shows a handset which includes a coaxial switch button 35 operating a sub-miniature micro-switch 36 via a cylindrical moulded seal. The switch is contained in a metal cylindrical sleeve 37 which supports the seal and ensures water tightness, even under pressure. This design permits the construction of an oscillatory system offering maximum operating flexibility with inherent reliability. Furthermore, there is no need for foot switches which, for the surgeon to be required to select one from a plurality of four differently tooled handsets, would involve impractical complications.

Three further tool-bit embodiments are shown as special-purpose modifications of the embodiments of FIGS. 1 and 3, in sets of FIGS. 8, 8A and 8B, FIGS. 9, 9A and 9B, and FIGS. 10, 10A and 10B, respectively. The embodiment of FIG. 8 differs from FIG. 1 essentially only in the fact that the outer surface 6' of the flanged tool element 40 is frustoconical, with a slope that converges in the proximal direction, thus providing a rake angle $\alpha_3$, proximally behind the distal circular cutting edge 5. In conjunction with the distally facing annular recess 12, the rake angle is suitably in the range 20° to 25° and enables the tool $\alpha_3$ element 40, when ultrasonically driven, to more effectively carve plastics cement via a laterally displacing course of distally directed displacement. Material thus excavated first accumulates transiently in recess 12 and is then forced in the proximal direction, as a migrating flow through passages 13, for accumulation and later removal from the space behind the flanged region of the tool element.

The tool bit or element 41 of FIG. 9 is again in many respects similar to that of FIG. 1 or of FIG. 8, except that the outer surface 6" of the flanged part of the tool element is frustoconical with a slope $\alpha_4$ which is suitably 20° to 25° and which converges in the distal direction. In FIG. 9A, the circular cutting edge 5' is proximally directed, and there is no distally directed cutting edge, although a plurality of spaced longitudinal passages will afford a path for rearward flow of such melted plastic as remains after use of the slope $\alpha_4$ to radially outwardly drive plastics melt into more solidly, intimately and secure engagement with the inner wall surface of bone (e.g., a femur) which is to receive an inserted prosthetic appliance. Since there is in FIG. 9 no distally facing annular recess (as at 12 in FIG. 1), a proximally facing annular recess 42 may provide an enlarged reservoir for plastic melt that accumulates via passages 13.

The tool element 43 of FIG. 10 has plural angularly spaced groove cutting arms, which happen to be two (44, 44') in number, extending in diametrically opposite directions. As best seen in FIG. 10A, each arm features a distally-directed cutting edge 44' at the radially outer limit of the arm, as well as, a distally facing concavity 45 which blends in transition to the generally conical distal end of the tool element. The use of tool element 43 will be seen to generate one (or possibly two) longitudinal grooves in plastics material, and of more pronounced depth than would be the case in use of the tool element of FIGS. 3 and 4; again, longitudinal passages 13' in each of these arms permit excavated and melted plastics material to migrate rearward, out of the way of groove-cutting action.

FIG. 11 is a schematic diagram of circuitry for driving any one of the various embodiments that have been described. In FIG. 11, the handset 50, as in FIGS. 5 and 7, is seen to comprise the piezoelectric driver 51 and a fitted tool bit or element 52, as well as a manual push-button on/off switch 53. At 54, a relay serves to enable a voltage-controlled oscillator (VCO) at 55, the output of which is amplified at 56 and fed to an impedance-matching network 57, connected in turn to the piezoelectric means 51. The signal supplied to the piezoelectric means is subject to feedback control via line 58 from the impedance-matching network to a phase-locked loop forming a component of the voltage-controlled oscillator at 55. The phase-locked loop will be understood to widen the frequency band over which mechanical resonance can be effected in the tool bit 52, for a range which is self-adapting to the impedance changes encountered by the tool bit as a function of the plastics-melting load variations to which it is subjected in the course of use.

What is claimed is:

1. A tool element for removal of bone-cementing plastics material, comprising an elongate shaft adapted for longitudinal transmission of ultrasonic energy from a proximal excitation end to a plastics-engaging working-head formation at the distal end of said shaft, said working-head formation comprising an annular body having a circumferentially continuous outer surface of diameter exceeding that of said shaft and integrally formed with said shaft, said annular body being defined by and between an axially spaced distal limit and a proximally spaced proximal limit, such that the distal limit of said outer surface has in a longitudinal section an acute angle defined by a distally directed circumferentially continuous distal cutting edge, said working-head formation having a central bore-centering distal-end formation, said bore-centering distal end formation extending from a base end that is axially between the proximal and distal limits of said annular body, and said bore-centering distal-end formation extending distally from said base end and distally beyond the distal limit of said annular body and at such radially inward offset from the outer surface of said annular body that a distally open annular concavity is defined adjacent said distal cutting edge and within said annular body, with angularly spaced longitudinal passages in the region of said annular concavity, for flowing distally melted plastic via said passages from said annular concavity and to the proximal side of said annular body.

2. In combination, a tool element as in claim 1 and ultrasonic driving means therefor, said driving means comprising piezo-electric transducer means operatively connected through a work horn to said shaft to cause said plastics-engaging end to vibrate ultrasonically and thereby to heat locally said plastics material, cavity means adapted to receive said heated plastics material, means to communicate said cavity means with a working zone adjacent said work surface, and excitation means for driving said transducer means, said excitation means including a voltage-controlled oscillator, an impedance-matching network electrically interposed between said oscillator and said transducer, said oscillator including a phase-locked loop, and a feedback connection from said impedance-matching network to said phase-locked loop.

3. The tool of claim 2, wherein said transducer means, said work horn and said work surface are components of a handset flexibly connected to said excitation means and having a manually operated control switch operatively connected to said excitation means.

4. A tool element for removal of bone-cementing plastics material comprising an elongate shaft adapted for longitudinal transmission of ultrasonic energy from a proximal excitation end to a distal plastics-engaging end, said plastics-engaging and comprising an annular body having a circumferentially continuous outer surface of outer diameter exceeding that of said shaft and integrally formed with said shaft, said annular body being defined by and between a distally spaced distal limit and a proximally spaced proximal limit, such that the distal limit of said outer surface has in a longitudinal section an acute angle defined by a distally directed circumferentially continuous distal cutting edge, and a bore-centering distal-end formation extending from a base end that is axially between the proximal and distal limits of said annular body and at radially inward offset from the outer surface of said annular body such that a distally open annular concavity is defined adjacent said distal cutting edge and within said annular body, with angularly spaced longitudinal passages in the region of said annular concavity, for flowing distally melted plastic via said passages from said concavity and to the proximal side of said annular body.

5. A tool element as in claim 1, wherein said circumferentially continuous outer surface is frusto-conical, with convergence in the proximal direction.

6. A tool element as in claim 1, wherein said circumferentially continuous outer surface is frusto-conical, with convergence in the distal direction.

7. A tool element as claimed in claim 5, wherein said frusto-conical outer surface slopes at an acute angle between 20° and 35° with respect to central longitudinal axis of said shaft.

8. A tool element as in claim 1, in which said bore-centering distal-end formation is conical.

9. A tool element for removal of bone-cementing plastics material, comprising an elongate shaft adapted for longitudinal transmission of ultrasonic energy from a proximal excitation end to a distal plastics-engaging end, said plastics-engaging end comprising an annular body having a circumferentially continuous outer surface of diameter exceeding that of said shaft and integrally formed with said shaft, said annular body being defined by and between an axially spaced distal limit and a proximally spaced proximal limit, such that the distal limit of said outer surface has in a longitudinal section an acute angle defined by a distally directed circumferentially continuous distal cutting edge, and an arcuate conical bore-centering end formation convergent distally beyond said annular body, said bore-centering end formation extending from a base end that is axially between the proximal and distal limits of said annular body and at radially inward offset from the outer surface of said annular body such that a distally open annular concavity is defined adjacent said distal cutting edge and within said annular body, with angularly spaced longitudinal passages in the region of said annular concavity, for flowing distally melted plastic via said passages from said annular concavity and to the proximal side of said annular body.

10. A tool element for removal of bone-cementing plastics material, comprising an elongate shaft adapted for longitudinal transmission of ultrasonic energy from a proximal excitation end to a distal plastics-engaging end, said plastics-engaging end comprising, about a central axis, an annular body of outer diameter exceeding that of said shaft and integrally formed with said shaft, and a circumferentially continuous arcuate conical bore-centering end formation convergent distally from and beyond a base at said annular body, said annular body being defined by and between an axially spaced distal limit and a proximally spaced proximal limit, such that the proximal limit of said outer surface has in a longitudinal section an acute angle defined by a proximally directed circumferentially continuous proximal cutting edge, said annular body (1) having a circumferentially continuous frusto-conical outer surface which converges distally to said base and (2) having a proximally open annular concavity having an axial depth which extends distally from said proximal limit, and said concavity having a radially outer limit of intersection with the proximal end of the frustoconical outer surface of said body, to define the acute angle of said cutting edge.

11. A tool for use in melting removal of plastics material from a hole, said tool comprising piezo-electric transducer means and an elongate shaft operatively and proximally coupled to said transducer means for distally remote delivery of ultrasonic energy from said transducer means to a plastics-engaging working-head formation at the distal end of said shaft, said working-head formation comprising an annular body having a circumferentially continuous outer surface of diameter exceeding that of said shaft and integrally formed with said shaft, said annular body having a circumferentially continuous outer surface which is defined by a distal axial limit that is axially spaced from a proximal axial limit, said working-head formation having a circumferentially continuous cutting edge at one of said axially spaced limits and an axially facing circumferentially continuous annular concavity radially adjacent and axially within said one limit such that said one limit of said outer surface has in a longitudinal section an acute angle defined by said circumferentially continuous cutting edge, and said working-head formation having a circumferentially continuous arcuate conical bore-centering distal-end formation convergent distally beyond the distal limit of said outer surface.

12. A tool element for removal of bone-cementing plastics material, comprising an elongate shaft adapted for longitudinal transmission of ultrasonic energy from a proximal excitation end to a distal plastics-engaging end, said plastics-engaging end comprising an annular body having a circumferentially continuous outer surface of diameter exceeding that of said shaft and integrally formed with said shaft, said annular body being defined by and between an axially spaced distal limit and a proximally spaced proximal limit, such that the distal limit of said outer surface has in a longitudinal section an acute angle defined by a distally directed circumferentially continuous distal cutting edge, and a conical bore-centering end formation convergent distally beyond said annular body, said bore-centering end formation extending from a base end that is axially between the proximal and distal limits of said annular body and at radially inward offset from the outer surface of said annular body such that a distally open annular concavity is defined adjacent said distal cutting edge and within said annular body, with angularly spaced longitudinal passages in the region of said annular concavity, for flowing distally melted plastic via said passages from said annular concavity and to the proximal side of said annular body.

13. A tool element as claimed in claim 12, wherein the outer surface of said annular body is generally cylindrical and said cutting edge is circular.

14. A tool element as claimed in claim 13, wherein said circular cutting edge is defined by intersection of a distally facing conical concave surface of said body at intersection with said generally cylindrical outer surface.

15. A tool element as claimed in claim 14, wherein the concave conical surface of said body intersects the cylindrical surface of said body at an angle between 20° and 25°.

16. A tool element as claimed in claim 8, wherein said passages are at least to a degree convergent in the proximal direction.

17. A tool element as claimed in claim 12, wherein at least one groove-cutting fin projects radially outward of said annular body.

18. A tool element as claimed in claim 17, wherein said groove-cutting fin is one of a plurality of angularly spaced groove-cutting fins extending radially outwardly of said annular body.

19. A tool element as claimed in claim 12, in which said distally open annular concavity fully determines the distally open ends of said passages.

20. A tool element for removal of bone-cementing plastics material, comprising an elongate shaft adapted for longitudinal transmission of ultrasonic energy from a proximal excitation end to a distal plastics-engaging end, said plastics-engaging end comprising, about a central axis, an annular body of outer diameter exceeding that of said shaft and integrally formed with said shaft, and a circumferentially continuous conical bore-centering end formation convergent distally from and beyond a base at said annular body, said annular body being defined by and between an axially spaced distal limit and a proximally spaced proximal limit, such that the proximal limit of said outer surface has in a longitudinal section an acute angle defined by a proximally directed circumferentially continuous proximal cutting edge, said annular body (1) having a circumferentially continuous frusto-conical outer surface which converges distally to said base and (2) having a proximally open annular concavity having an axial depth which extends distally from said proximal limit, and said concavity having a radially outer limit of intersection with the proximal end of the frustoconical outer surface of said body, to define the acute angle of said cutting edge.

21. A tool element as claimed in claim 20, in which said annular concavity has a radially inner limit having substantial tangency with said shaft at juncture with said body.

22. A tool element as claimed in claim 20, in which said concavity is of arcuate profile in a longitudinal section through said tool element.

23. A tool element as claimed in claim 20, in which said frustoconical surface establishes an acute-angle relationship with the central axis in a longitudinal section through said tool element.

24. A tool element as claimed in claim 23, in which said angle is in the range between 20° and 25°.

25. A tool element as claimed in claim 20, in which said concavity establishes an acute-angle relationship with the outer surface of said body at intersection with the proximal end of the frusto-conical outer surface of said body, said angle being taken in a longitudinal section through said tool element.

26. A tool element as claimed in claim 16, in which said angle is in the range between 20° and 25°.

27. A tool for use in melting removal of plastics material from a hole, said tool comprising piezoelectric transducer means and an elongate shaft operatively and proximally coupled to said transducer means for distally remote delivery of ultrasonic energy from said transducer means to a plastics-engaging working-head formation at the distal end of said shaft, said working-head formation comprising an annular body having a circumferentially continuous outer surface of diameter exceeding that of said shaft and integrally formed with said shaft, said annular body having a circumferentially continuous outer surface which is defined by a distal axial limit that is axially spaced from a proximal axial limit, circumferentially continuous distal and proximal limits, said outer surface exceeding the diameter of the distal end of said shaft, said working-head formation having a circumferentially continuous cutting edge at one of said axially spaced limits and an axially facing circumferentially continuous annular concavity radially adjacent and axially within said one limit such that said one limit of said outer surface has a longitudinal section an acute angle defined by said circumferentially continuous cutting edge, and said working-head formation having a circumferentially continuous conical bore-centering distal-end formation convergent distally beyond the distal limit of said outer surface.

28. The tool of claim 27, wherein said one limit having said circumferentially continuous cutting edge is the distal limit of said circumferentially continuous outer surface.

29. The tool of claim 27, wherein said one limit having said circumferentially continuous cutting edge is the proximal limit of said circumferentially continuous outer surface.

30. The tool element of claim 12, and a handset enclosure containing piezo-electric transducer means operatively connected to the proximal end of said shaft, said piezo-electric transducer means being sealingly encased in a first enclosure of waterproof plastics material and exterior thereof a second enclosure of stainless steel.

31. The tool element of claim 12, and piezo-electric transducer means connected via a work horn to the proximal end of said shaft.

* * * * *